United States Patent [19]

Ohsugi et al.

[11] Patent Number: 4,542,154
[45] Date of Patent: Sep. 17, 1985

[54] ANTIBIOTIC COMPOUND

[75] Inventors: Katsuhisa Ohsugi, Iwaki; Junji Ichida, Kodaira; Eisaku Takahashi, Iwaki, all of Japan

[73] Assignee: Kureha Kagaku Kogyo Kabushiki Kaisha, Nihonbashi, Japan

[21] Appl. No.: 512,138

[22] Filed: Jul. 8, 1983

[30] Foreign Application Priority Data

Jul. 23, 1982 [JP] Japan .................................. 57-128693
Aug. 3, 1982 [JP] Japan .................................. 57-135557

[51] Int. Cl.$^4$ .................. A61K 31/335; C07D 303/38
[52] U.S. Cl. .................................... 514/475; 549/545; 435/119; 435/254; 435/933
[58] Field of Search .......................... 549/545; 424/278

Primary Examiner—Norma S. Milestone
Attorney, Agent, or Firm—Wegner & Bretschneider

[57] ABSTRACT

A novel antibiotic compound 3-(6-isocyano-3,7-dioxatricyclo[4.1.0.0$^{2,4}$]hept-4-yl)propenoic acid is produced by a newly isolated microorganism belonging to the genus Penicillium.

2 Claims, 4 Drawing Figures

ANTIBIOTIC COMPOUND

The present invention relates to a novel antibiotic, namely 3-(6-isocyano-3,7-dioxatricyclo[4.1.0.0$^{2,4}$]hept-4-yl)propenoic acid, a method of preparation thereof using a newly isolated microorganism belonging to the genus Penicillium and a therapeutic or disinfectant drug containing the antibiotic.

It was already known that a certain mold belonging to the genus Penicillium produces an antibiotic, for example penicillin, griseofulvin, antibiotic SL-3238, cyanenin, funiculosin, gliotoxin, janthinillin, mycophenolic acid, negapillan, palitantin, viridicatin, wortmannin or the like.

It has now been found that a newly isolated mold belonging to the genus Penicillium produces an antibiotic which has physicochemical properties and an antibacterial spectrum different from those of known antibiotics.

It is an object of the present invention to provide a novel antibiotic (hereinafter referred to Antibiotic No. 2188).

An another object of the invention is to provide a biological method for preparing the Antibiotic No. 2188.

A still another object is to provide a newly isolated strain belonging to the genus Penicillium which is capable of producing the Antibiotic No. 2188.

A still further object of the invention is to provide a medicament containing the Antibiotic No. 2188.

Among the attached drawings.

Figure 1:
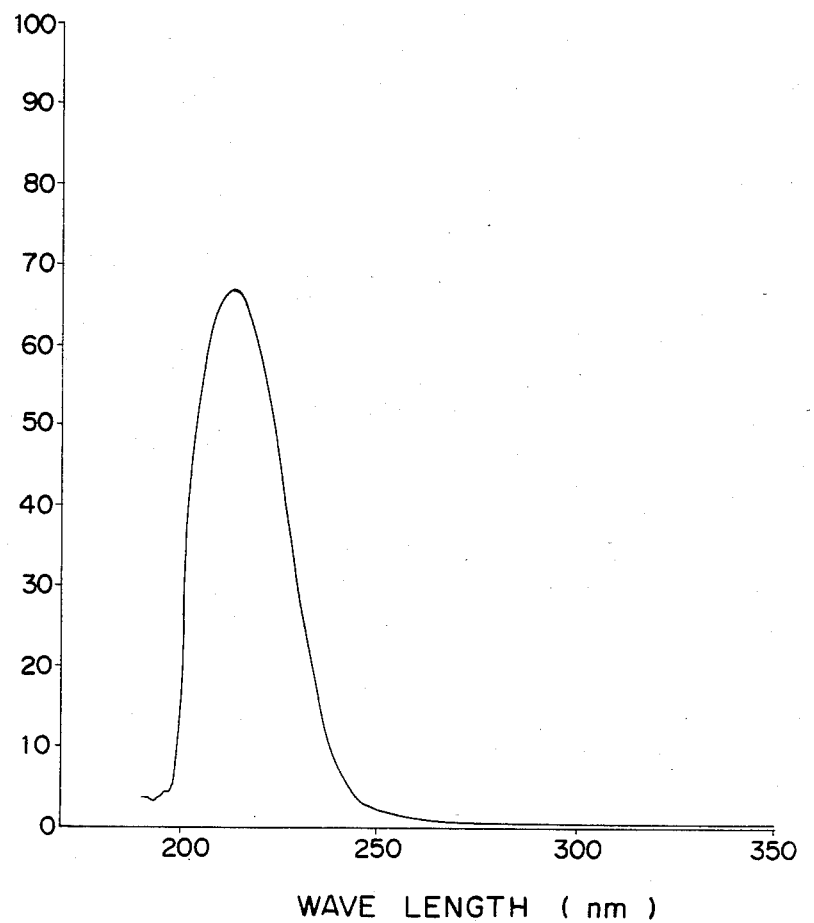
FIG. 1 shows an ultraviolet absorption spectrum of Antibiotic No. 2188.

The novel Antibiotic No. 2188 of the invention is 3-(6-isocyano-3,7-dioxatricyclo[4.1.0.0$^{2,4}$]hept-4-yl)propenoic acid which may also be called as 3-(1-(1,2-3,4-diepoxy-4-isocyanocyclopentyl))propenoic acid. This compound has the following formula:

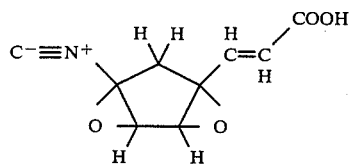

Antibiotic No. 2188 may be obtained from a cultured medium of a strain belonging to the genus Penicillium. The process for preparing Antibiotic No. 2188 is also included within the scope of the invention.

The process of the invention comprises aerobically cultivating a mold belonging to the genus Penicillium on an appropriate medium and collecting a desired product from the cultured medium. Preferable mold to be used in the invention is a newly isolated strain from a soil which has been deposited to Fermentation Research Institute, Agency of Industrial Science and Technology, Ministry of International Trade and Industry, Japan, under No. 142 (FERM BP-142). It will be understood for a man skilled in the art that a mutant of FERM BP-142 and related fungi may also be preferably applied to the process of the present invention if they are capable of producing Antibiotic No. 2188.

The newly isolated microorganism per se is also included in the scope of the invention. The newly isolated mold FERM BP-142 has the mycological properties set forth below.

| Growth on various media | |
| --- | --- |
| Malt extract agar | good |
| Potato dextrose agar | good |
| Sabouraud agar | good |
| Oatmeal agar | good |
| YpSs agar | good |
| Glucose dry yeast agar | good |
| Mucor-synthetic medium | restrictedly |
| Czapek agar | poor |

The colony is generally velvety at 30° C. and woolly at 20° C.; dull yellow-green, light green, light grey-green or grey-grey depending onto the type of culture medium; dark green conidia; yellow or orange-yellow mycelia; the reverse of colony is yellow-orange or orange-red; no growth at 37° C.

MORPHOLOGY

Conidiophore: directly grows from creeping hypha and aerial hypha; 2.5–3.0×100–300 μm; smooth or slightly rough surface of wall;

Penicillus: biverticillate symmetrical;

Metula: 2.5–3.5×7.5–15 μm; a bundle of 3–6 metulae;

Phialide: typically lanceolate; 2.0–3.8×7.5–13 μm; in clusters of 2–6 elements in the verticil;

Conidium: elliptical; 2.5–3×3–3.8 μm; green; smooth wall; tangled or parallel chains.

The newly isolated strain of the invention has thus been identified with a strain of *Penicillium rugulosum* described in "A Manual of the Penicillia" by K. B. Raper and C. Thom, the Williams and Wilkins Company, 1949.

The microorganism capable of producing Antibiotic No. 2188 of the invention may be subcultured by transfer on a culture medium comprising 0.1% of yeast extract, 0.1% of beef extract, 0.2% of peptone, 1% of glucose and 2% of agar, for example.

For a culture method of the mold in the process of the invention may be used any conventional aerobic culture for a microorganism, for example, solid culture, shaking culture or submerged culture. The microorganism producing Antibiotic No. 2188 grows ordinarily at 10°–35° C., preferably 20°–30° C.

Any known nutrient for a culture of fungi or other microorganisms may be used in the process of the invention. For example, glucose, maltose, dextrin, starch, lactose, sucrose or glycerin may be usable for a carbon source. On the other hand, for a nitrogen source in the process of the invention may be used any known nutrient such as peptone, beef extract, yeast, yeast extract, soybean flour, peanut flour, cotton seed dregs, corn steep liquor, rice bran and inorganic nitrogen.

A culture medium for production of Antibiotic No. 2188 may contain, if necessary, inorganic salt and/or metal salt. In addition, it may contain a small amount of heavy metal or other additive such as other nutrient and growth accelerating substance. The medium may also contain antifoam agent such as silicone oil and surfactant if the generation of foam is necessary to be prevented.

The microorganism is cultivated for a suitable period so that Antibiotic No. 2188 is substantially produced in the medium and accumulates in a sufficient amount. The desired product is collected from the medium in such a manner as shown in Examples, that is, an appropriate combination of means such as extraction with an organic solvent for example ether, chloroform, ethyl acetate, butyl acetate or butanol, dissolution into a polar solvent for example acetone or alcohol, removal of impurities with a non-polar solvent for example petroleum ether or hexane, gel filtration by Sephadex column, adsorption chromatography by active carbon or silica gel and ion-exchange chromatography.

The compound of the invention, Antibiotic No. 2188, shows an antibacterial activity against various gram-positive and gram-negative bacteria. On the other hand, Antibiotic No. 2188 showed no acute toxicity to mouse administered intaperitoneally in a dose rate of 100 mg/kg.

Antibiotic No. 2188 may be directly applicable to human and animals as an antibacterial and/or disinfectant medicament. The medicament may preferably be a composition combined with a pharmaceutically acceptable carrier compatible with the compound of the present invention.

The carrier usable in the invention is an organic or inorganic inert substance suitable for intraintestinal, oral or parenteral administration, for example, water, gelatine, gum arabic, lactose, starch, magnesium stearate, talc, vegetable oil, polyalkylene glycol, yellow petrolatum or the like.

The dosage form of the pharmaceutical composition of the invention may be solid such as tablet, sugar-coated pellet, suppository and capsule, semi-solid such as ointment, or liquid such as solution, suspension and emulsion. The composition may further contain one or more adjuvants such as a preservative, stabilizer, wetting agent, emulsifier, buffer solution and salt for adjusting the osmotic pressure.

The invention will be illustrated in more detail by the following non-limitative Examples.

EXAMPLE 1

A slant agar culture of a strain (FERM BP-142) of *Penicillium rugulosum* was inoculated on 100 ml of Bennett's medium (0.1% of yeast extract, 0.1% of beef extract, 0.2% of N.Z. amine type-A (Sheffield Chemical Co., San Ramon, CA 94583, USA) and 1% of glucose, pH of 7.2) in a 300 ml Erlenmeyer flask. The culture media in fifty flasks were cultivated at 24° C. for 72 hours on a rotary shaker with 180 rpm.

The resultant culture (5 l in total) was cultivated at 24° C. for 60 hours on 100 l of a sterilized medium in a 200 l fermentor with aeration of purified air at the rate of 50 l/min and agitation of 200 rpm. The composition of the sterilized medium was;

| soluble starch | 1.5% |
|---|---|
| glycerin | 1.5% |
| cotton seed dregs | 1.0% |
| soybean flour | 1.0% |
| yeast extract | 1.0% |
| $K_2HPO_4$ | 0.7% |
| $MgSO_4 \cdot 7H_2O$ | 0.05% |
| $CoCl_2 \cdot 5H_2O$ | 0.001% |
| antifoam (ADEKANOL LG 126, ASAHI DENKA KOGYO K.K.) | 0.1% |

The whole culture (100 l) was passed through a Sharpless (type JP-U 122-1, TOMOE ENGINEERING Co.) and a Delabal (type BRP X 309-355-60, Sweden) to remove mycelial cake. Clean supernatant was adjusted to a pH of 4 with hydrochloric acid and extracted with a fifty by volume of ethyl acetate by a continuous centrifugal extraction apparatus (type C-1333, Hitachi Ltd.). The extract was concentrated by a condenser, and the concentrate was then subjected to back extraction with an aqueous 1% solution of sodium bicarbonate. The aqueous phase was adjusted to a pH of 4.0 with hydrochloric acid and extracted with ethyl acetate. The extract was dried on anhydrous sodium sulfate and evaporated at less than 40° C. under vacuum to obtain a crude product.

The crude product was passed through a column of active carbon, placed on the top of a column (4 cm in diameter and 50 cm in height) filled with silica gel (WAKOGEL Q 23, Wako Chemicals Co.) and developed with ethyl acetate-chloroform (1:19 by volume) to elute the active fraction to which n-hexane was then added to obtain 3 g of white powder.

Figure 2:
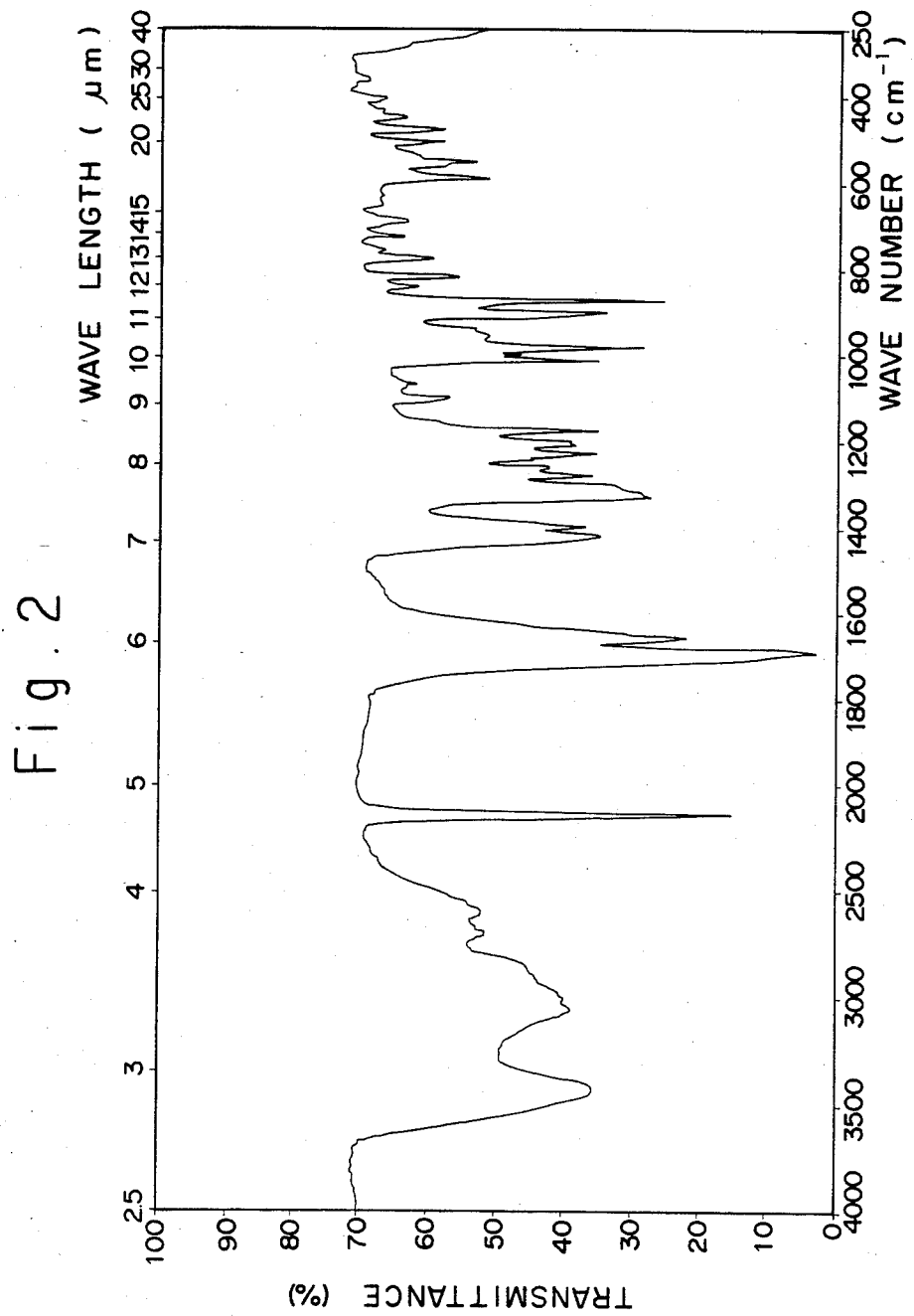
FIG. 2 is an infrared absorption spectrum of Antibiotic No. 2188.
Figure 3:
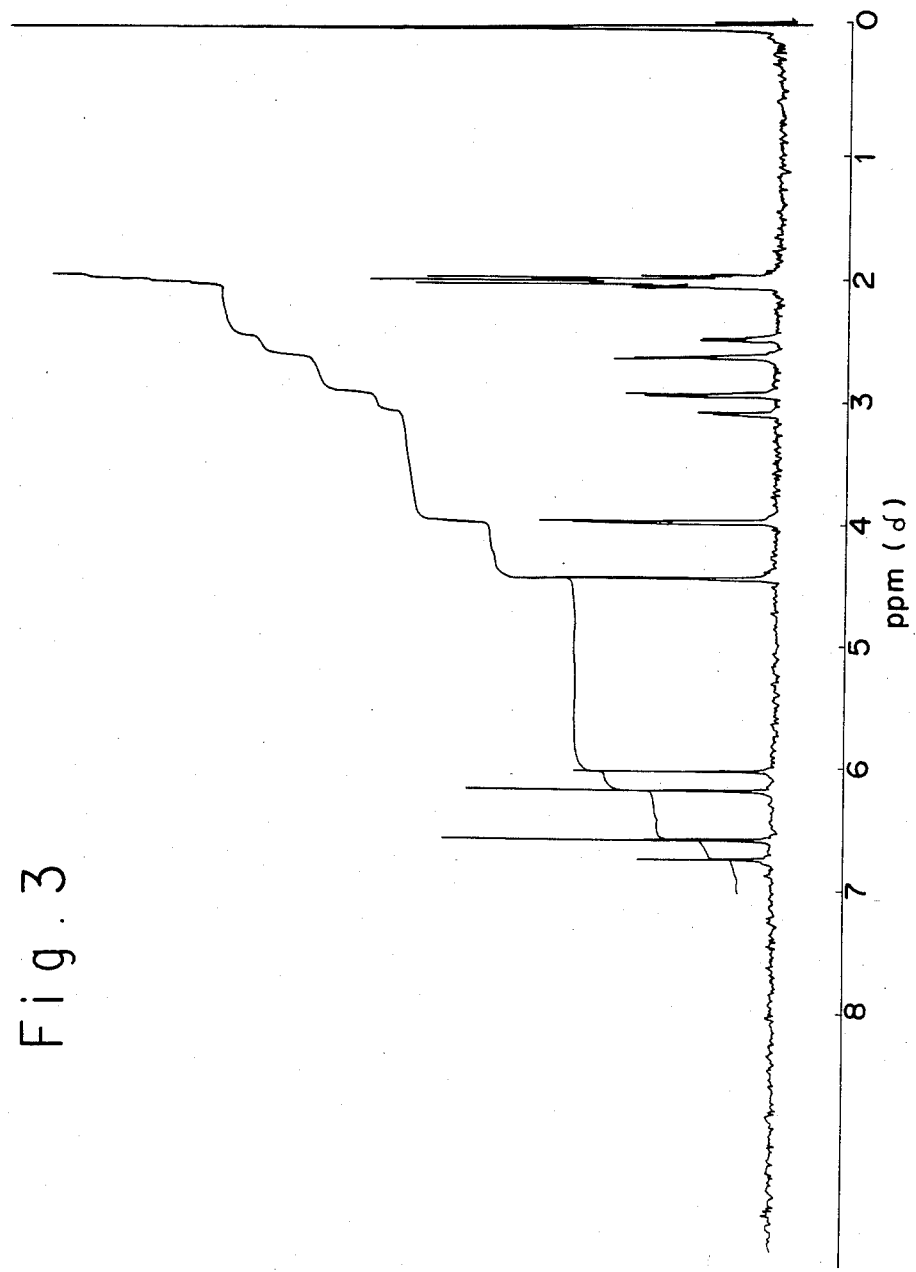
FIGS. 3 and 4 show a proton and carbon-13 nuclear magnetic resonance spectra of Antibiotic No. 2188, respectively.
Figure 4:
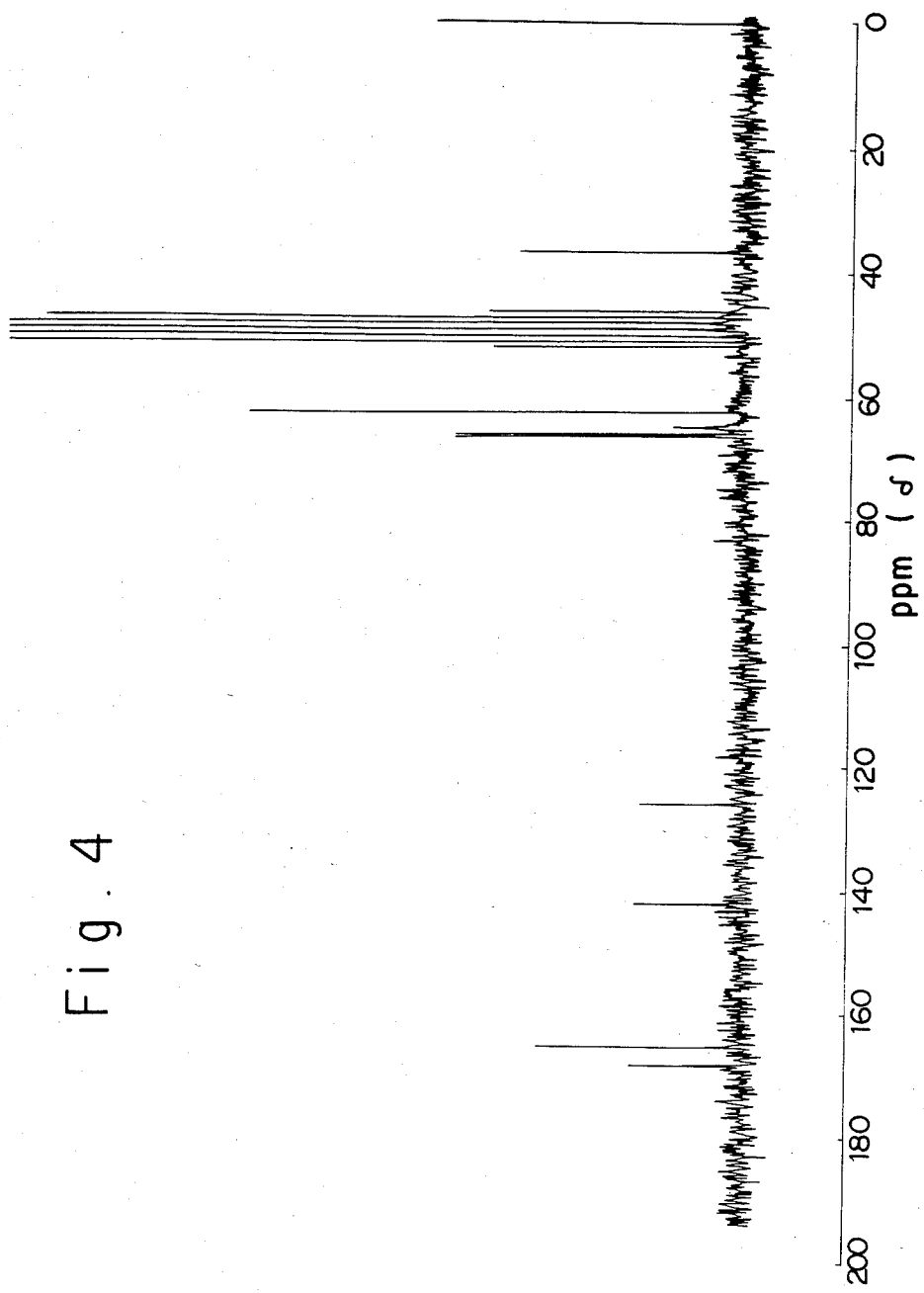

The product obtained has the physicochemical properties set forth below:

| elementary analysis; $C_9H_7NO_4$(%) | | | | |
|---|---|---|---|---|
| | C | H | N | O |
| found; | 56.35, | 3.49, | 7.34, | 32.82 | molecular weight estimated by mass spectrometry; 193 melting point; 135°–136° C. (decomposition)

specific rotatory power;

$[\alpha]_D^{20} = -128.8$ (c=1.0% in ethyl acetate)

ultraviolet absorption spectrum (see FIG. 1);

$\lambda_{max}^{methanol} = 215$ nm ($\epsilon = 14378$)

infrared absorption spectrum in KBr (see FIG. 2); 3450, 3000, 2150, 1700, 1665, 1425, 1330, 1090, 980, 900, 875.

proton nuclear magnetic resonance spectrum in deuterated acetone (see FIG. 3);

δ(ppm); 2.55 (d, d, 1H, J=16, J=1.0); 3.05 (d, d, 1H, J=16, J=0.5); 3.98 (d, 1H, J=1.0); 4.45 (d, 1H, J=0.5); 6.11 (d, 1H, J=16); 6.71 (d, 1H, J=16).

carbon-13 unclear magnetic resonance spectrum in deuterated methanol (see FIG. 4);

δ(ppm); 168.1 (s), 165.1 (s), 141.9 (d), 125.8 (d), 66.4 (d), 66.1 (d), 64.9 (s), 62.5 (s), 36.6 (t).

soluble in methanol, ethanol, acetone, ethyl acetate, chloroform and benzene.

insoluble in hexane and petroleum ether thin-layer chromatography by silica gel (Kieselguhr G, Merck); only one spot at

| Rf = 0.62 in chloroform-ethyl acetate-acetic acid (10:10:1) |
|---|
| 0.44 in chloroform-ethyl acetate-acetic acid (10:10:0.2) |
| 0.79 in n-butanol-acetic acid-water (4:1:1) | reversed thin-layer chromatography by KC-18 (Watmann); only one spot at

Rf = 0.86 in methanol-water (4:1)
0.94 in propanol-water (4:1)

EXAMPLE 2

The following microorganisms were tested by the agar-dilution method using nutrient agar medium to determine the antibacterial spectrum of the product obtained in Example 1. The results are set forth below.

| Microorganism | MIC (μg/ml) |
| --- | --- |
| Staphylococcus aureus 209 p | 6.25 |
| Bacillus subtilis PCI 219 | 12.5 |
| Streptococcus pyogenes IFO 3340 | 6.25 |
| Micrococcus luteus PCI 1001 | 6.25 |
| Corynebacterium faciens IAM 1079 | 12.5 |
| Corynebacterium equi IFO 3730 | 6.25 |
| Micrococcus lysodeikticus | 6.25 |
| Mycobacterium avium IFO 3082 | 12.5 |
| Escherichia coli K-12 IAM 1264 | 12.5 |
| Klebsiella pneumoniae IFO 12015 | 50 |
| Citrobacter freundii IFO 12681 | 12.5 |
| Proteus vulgaris IFO 3167 | 12.5 |
| Proteus mirabilis IFO 3849 | 50 |
| Proteus morganii IFO 3168 | 12.5 |
| Proteus inconstans IFO 12930 | 50 |
| Pseudomonas aeruginosa IFO 3080 | 100 |
| Pseudomonas fluorescens IFO 3903 | 12.5 |
| Pseudomonas putida T-2 | 6.25 |
| Pseudomonas ovalis | >100 |
| Vibrio metshnikov IAM 1039 | 1.6 |
| Vibrio tyrogenes IAM 1080 | 3.1 |
| Salmonella abortusequi ATCC 9842 | 12.5 |
| Salmonella anatum 1 | 12.5 |
| Aerobacter aerogenes ATCC 8724 | 50 |
| Erwinia aroidae IAM 1068 | 25 |
| Xanthomonas oryzae IAM 1657 | 50 |
| Serratia marcescens IAM 1065 | >100 |
| Aspergillus niger IFO 6342 | >200 |
| Aspergillus fumigatus IAM 2155 | 100 |
| Aspergillus oryzae IAM 2732 | >200 |
| Penicillium funiculosum IFO 6345 | 200 |
| Saccharomyces cerevisiae | >200 |
| Candida albicans IAM 4905 | >200 |
| Trichophyton rubrum IFO 5467 | 50 |
| Trichophyton interdigitale | 100 |
| Epidermophyton floccosum IFO 9045 | 50 |
| Microsporum gypseum IFO 5948 | 100 |
| Bacteroides fragilis | 50 |
| Eubacterium aerofaciens | >200 |
| Peptococcus aerogenes | 25 |
| Peptostreptococcus micros | 25 |
| Peptostreptococcus parvulus | 50 |
| Bifidobacterium adolescentis | 200 |
| Fusobacterium necrophorum | 50 |
| Lactobacillus acidophilus | 200 |

EXAMPLE 3

Five Erlenmeyer flasks of 300 ml containing respectively 100 ml of a medium with a pH of 7.2 which comprises 1% of glucose, 0.1% of yeast extract, 0.1% of beef extract and 0.2% of polypeptone were sterilized under pressure. Spores from the slant agar culture of a mold (FERM BP-142) were respectively inoculated to the medium in the flasks and cultivated at 26° C. for 70 hours with shaking of 180 rpm. The obtained culture (500 ml) was inoculated onto 15 l of a sterilized medium with a pH of 7.0 in 30 l jar fermentor, and cultivated at 26° C. for 60 hours under aeration of purified air in the rate of 15 l/min and agitation of 300 rpm. The composition of the sterilized medium was;

| | |
| --- | --- |
| NaNO$_3$ | 0.3% |
| K$_2$HPO$_4$ | 0.1% |
| MgSO$_4$.7H$_2$O | 0.05% |
| KCl | 0.05% |
| FeSO$_4$.7H$_2$O | 0.001% |
| sucrose | 3% |
| yeast extract | 1% |
| antifoam (ADEKANOL LG 109) | 0.1%. |

The resultant culture was filtered by using Celite 545 as a filter aid. The filtrate was absorbed to a column of 4 cm in diameter and 50 cm in height filled with DIAION HP 20 (Mitsubishi Kasei Co. Ltd.), washed with water and eluted with 60% methanol. The eluate was concentrated under vacuum at less than 40° C. The concentrated material was extracted with ethyl acetate, and the extract was dried on anhydrous sodium sulfate and further concentrated under vacuum at less than 40° C.

The obtained liquid material was passed through a column (1.5 cm in diameter and 30 cm in height) filled with active carbon. The active fraction was concentrated under vacuum and the concentrated material was applied on a column (20 mm × 300 mm) of silica gel (WAKOGEL C 200, Wako Chemicals Co.) and was washed with chloroform. The column was developed with ethyl acetate-chloroform (1:19 by volume) to elute the active fraction to which n-hexane was added to obtain 200 mg of white powder. The obtained product showed the same physicochemical and biological properties as shown in Example 1.

What is claimed is:
1. 3-(6-isocyano-3,7-dioxatricyclo[4.1.0.0$^{2,4}$]hept-4-yl)-propenoic acid.
2. An antibacterial composition comprising an antibacterially effective amount of 3-(6-isocyano-3,7-dioxatricyclo[4.1.0.0$^{2,4}$]hept-4-yl)-propenoic acid and a pharmaceutical carrier.

* * * * *